(12) United States Patent
Block et al.

(10) Patent No.: US 6,440,967 B1
(45) Date of Patent: Aug. 27, 2002

(54) COMBINATION OF A GABA$_A$ ALPHA 5 INVERSE AGONIST AND COX-2 INHIBITOR, NSAID, ESTROGEN OR VITAMIN E

(75) Inventors: Gilbert A. Block, Ardmore; Christopher R. Lines, Philadelphia, both of PA (US)

(73) Assignee: Merck & Co., Inc., Rahway, NJ (US)

( * ) Notice: Subject to any disclaimer, the term of this patent is extended or adjusted under 35 U.S.C. 154(b) by 0 days.

(21) Appl. No.: 09/438,007

(22) Filed: Nov. 10, 1999

Related U.S. Application Data
(60) Provisional application No. 60/108,105, filed on Nov. 12, 1998.

(51) Int. Cl.⁷ ...................... A61K 31/53; A61K 31/485; A61K 31/50
(52) U.S. Cl. ........................................ 514/243; 514/252
(58) Field of Search ................................ 514/570, 252, 514/243

(56) References Cited

U.S. PATENT DOCUMENTS
5,434,170 A * 7/1995 Andrulis, Jr. ................ 514/323

FOREIGN PATENT DOCUMENTS
| | | | |
|---|---|---|---|
| GB | WO 98/50385 | * | 12/1998 |
| WO | WO98/04560 | | 2/1998 |
| WO | WO98/18792 | | 5/1998 |
| WO | WO98/24435 | | 6/1998 |

* cited by examiner

*Primary Examiner*—Theodore J. Criares
(74) *Attorney, Agent, or Firm*—Shu Muk Lee; David L. Rose

(57) ABSTRACT

Combinations of a GABA$_A$ alpha 5 inverse agonist and a COX-2 inhibitor, NSAID, estrogen or vitamin E are disclosed for treating neurodegenerative conditions such as Alzheimer's Disease.

4 Claims, No Drawings

COMBINATION OF A GABA$_A$ ALPHA 5 INVERSE AGONIST AND COX-2 INHIBITOR, NSAID, ESTROGEN OR VITAMIN E

This application claims the benefit of U.S. Patent Application No. 60/108,105, filed Nov. 12, 1998.

The present invention relates to a combination of a COX-2 inhibitor, NSAID, estrogen or vitamin E and an inverse agonist of the GABA$_A$ α5 receptor subtype, and the use of the combination in treating neurodegenerative conditions such as Alzheimer's Disease.

Alzheimer's Disease is a poorly understood neurodegenerative condition mainly affecting the elderly but also younger people who are generally genetically predispositioned to it.

In a first embodiment the present invention provides a new and surprisingly effective synergistic combination of a COX-2 inhibitor and an inverse agonist of the GABA$_A$ α5 receptor subtype for separate, sequential or simultaneous administration.

In a second embodiment the present invention provides a new and surprisingly effective synergistic combination of an NSAID and an inverse agonist of the GABA$_A$ α5 receptor subtype for separate, sequential or simultaneous administration.

In a third embodiment the present invention provides a new and surprisingly effective synergistic combination of an estrogen and an inverse agonist of the GABA$_A$ α5 receptor subtype for separate, sequential or simultaneous adminstration.

In a fourth embodiment the present invention provides a new and surprisingly effective synergistic combination of Vitamin E and an inverse agonist of the GABA$_A$ α5 receptor subtype for separate, sequential or simultaneous adminstration.

The present invention provides a greater than expected improvement in the condition of subjects suffering from a neurodegenerative with an associated cognitive deficit, such as Alzheimer's Disease or Parkinson's disease, or from a cognitive deficit which may arise from a normal process such as aging or from an abnormal process such as injury, than would be expected from administration of the active ingredients alone. Further, the combination allows for a lower overall dose of each of the active ingredients to be administered thus reducing side effects and decreasing any reduction in the effectiveness of each of the active ingredients over time.

Any inverse agonist of the GABA$_A$ α5 receptor subtype may be used which fulfills the criteria of WO-A-9625948. The inverse agonist may be either binding selective for the α$_5$ subtype or functionally selective, or both. Thus the inverse agonist is preferably an antagonist, or has insignificant agonist or inverse agonist properties at the other GABA$_A$ α receptor subtypes when measured in oocytes as described in WO-A-9625948.

Thus the inverse agonist preferably has a functional efficacy at the α$_5$ receptor subunit of less than –20% inverse agonism or greater, for example –30% and functional efficacies at the α$_1$, α$_2$ and α$_3$ receptor subunits of between –20 and +20%. By functional efficacy is meant the percentage modulation of the EC$_{20}$ response produced by GABA, upon coadministration of the inverse agonist, in oocytes expressing GABA$_A$ receptor channels containing the α receptor subunit under test. Details of this measurement are given in WO-A-9625948.

The inverse agonist preferably binds selectively to GABA$_A$ receptors containing the α$_5$ subunit 10, 25 and particularly 50 times compared to GABA$_A$ receptors subunits containing the α$_1$, α$_2$ or α$_3$ subunits. Preferably this binding selectivity is shown over all these subunits.

A preferred class of inverse agonists, which are disclosed in WO-A-9850385, are of formula I:

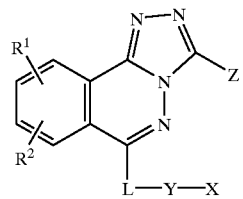

wherein:

$R^1$ is hydrogen, halogen or CN or a group $C_{1-4}$alkyl, $C_{2-4}$alkenyl, $C_{2-4}$alkynyl, $C_{1-4}$alkoxy, $C_{2-4}$alkenyloxy or $C_{2-4}$alkynyloxy, each of which groups is unsubstituted or substituted with one or two halogen atoms or with a pyridyl or phenyl ring each of which rings may be unsubstituted or independently substituted by one or two halogen atoms or nitro, cyano, amino, methyl or CF$_3$ groups;

$R^2$ is hydrogen, halogen or CN or a group $C_{1-4}$alkyl, $C_{2-4}$alkenyl, $C_{2-4}$alkynyl, $C_{1-4}$alkoxy, $C_{2-4}$alkenyloxy or $C_{2-4}$alkynyloxy each of which groups is unsubstituted or substituted with one or two halogen atoms;

L is O, S or NR$^n$ where R$^n$ is H, $C_{1-6}$alkyl or $C_{3-6}$cycloalkyl;

X is a 5-membered heteroaromatic ring containing 1, 2, 3 or 4 heteroatoms independently chosen from oxygen, nitrogen and sulphur, at most one of the heteroatoms being oxygen or sulphur, or a 6-membered heteroaromatic ring containing 1, 2 or 3 nitrogen atoms, the 5- or 6-membered heteroaromatic ring being optionally fused to a benzene ring and the heteroaromatic ring being optionally substituted by R$^x$ and/or R$^y$ and/or R$^z$, where R$^x$ is halogen, R$^3$, OR$^3$, OCOR$^3$, NR$^4$R$^5$, NR$^4$COR$^5$, tri($C_{1-6}$alkyl)silyl$C_{1-6}$alkoxy$C_{1-4}$alkyl, CN or R$^9$, R$^y$ is halogen, R$^3$, OR$^3$, OCOR$^3$, NR$^4$R$^5$, NR$^4$COR$^5$ or CN and R$^z$ is R$^3$, OR$^3$ or OCOR$^3$, where R$^3$ is $C_{1-6}$alkyl, $C_{2-6}$alkenyl, $C_{2-6}$alkynyl, $C_{3-6}$cycloalkyl, hydroxy$C_{1-6}$alkyl and R$^3$ is optionally mono-, di- or tri-fluorinated, R$^4$ and R$^5$ are each independently hydrogen, $C_{1-6}$alkyl, $C_{2-6}$alkenyl, $C_{2-6}$alkynyl, $C_{3-6}$cycloalkyl or CF$_3$ or R$^4$ and R$^5$, together with the nitrogen atom to which they are attached, form a 4–7 membered heteroaliphatic ring containing the nitrogen atom as the sole heteroatom, and R$^9$ is benzyl or an aromatic ring containing either 6 atoms, 1, 2 or 3 of which are optionally nitrogen, or 5 atoms, 1, 2 or 3 of which are independently chosen from oxygen, nitrogen and sulphur, at most one of the atoms being oxygen or sulphur, and R$^9$ is optionally substituted by one, two or three substituents independently chosen from halogen atoms and $C_{1-4}$alkyl, $C_{2-4}$alkenyl, $C_{2-4}$alkynyl, $C_{1-4}$alkoxy, $C_{2-4}$alkenyloxy and $C_{2-4}$alkynyloxy groups each of which groups is unsubstituted or substituted by one, two or three halogen atoms, and when X is a pyridine derivative, the pyridine derivative is optionally in the form of the N-oxide and providing that when X is a tetrazole derivative it is protected by a $C_{1-4}$alkyl group; or X is phenyl optionally substituted by one, two or three groups independently selected from halogen, cyano, $C_{1-6}$alkyl, $C_{2-6}$alkenyl, $C_{2-6}$alkynyl and $C_{3-6}$cycloalkyl;

Y is optionally branched $C_{1-4}$alkylidene optionally substituted by an oxo group or Y is a group (CH$_2$)$_j$O wherein the oxygen atom is nearest the group X and j is 2, 3 or 4;

Z is a 5-membered heteroaromatic ring containing 1, 2 or 3 heteroatoms independently selected from oxygen, nitrogen and sulphur, at most one of the heteroatoms being oxygen or sulphur and providing that when two of the heteroatoms are nitrogen an oxygen or sulphur atom is also present and that when one of the atoms is oxygen or sulphur then at least one nitrogen atom is present, or a 6-membered heteroaromatic ring containing 2 or 3 nitrogen atoms, Z being optionally substituted by $R^v$ and/or $R^w$, where $R^v$ is halogen, $R^6$, $NR^7R^8$, $NR^7COR^8$, CN, furyl, thienyl, phenyl, benzyl, pyridyl or a 5-membered heteroaromatic ring containing at least one nitrogen atom and optionally 1, 2 or 3 other heteroatoms independently selected from oxygen, nitrogen and sulphur, at most one of the other heteroatoms being oxygen or sulphur and $R^w$ is $R^6$ or CN;

$R^6$ is $C_{1-6}$alkyl, $C_{2-6}$alkenyl, $C_{2-6}$alkynyl, $C_{3-6}$cycloalkyl, hydroxy$C_{1-6}$alkyl, $C_{1-6}$alkoxy, $C_{2-6}$alkenyloxy, $C_{2-6}$alkynyloxy, $CH_2F$ or $CF_3$; and $R^7$ and $R^8$ are each independently hydrogen, $C_{1-6}$alkyl, $C_{2-6}$alkenyl, $C_{2-6}$alkynyl, $C_{3-6}$cycloalkyl or $CF_3$ or $R^7$ and $R^8$, together with the nitrogen atom to which they are attached, form a 4–7 membered heteroaliphatic ring containing the nitrogen atom as the sole heteroatom;

or a pharmaceutically acceptable salt thereof.

As used herein, the expression "$C_{1-6}$alkyl" includes methyl and ethyl groups, and straight-chained and branched propyl, butyl, pentyl and hexyl groups. Particular alkyl groups are methyl, ethyl, n-propyl, isopropyl and t-butyl. Derived expressions such as "$C_{1-4}$alkyl", "$C_{2-4}$alkenyl", "$C_{2-6}$alkenyl", "hydroxy$C_{1-6}$alkyl", "$C_{2-4}$alkyl" and "$C_{2-6}$alkynyl" are to be construed in an analogous manner.

The expression "$C_{3-6}$cycloalkyl" as used herein includes cyclic propyl, butyl, pentyl and hexyl groups such as cyclopropyl and cyclohexyl.

Suitable 5- and 6-membered heteroaromatic rings include pyridinyl, pyridazinyl, pyrimidinyl, pyrazinyl, pyrrolyl, pyrazolyl, oxazolyl, isoxazolyl, thiazolyl, isothiazolyl, imidazolyl, oxadiazolyl and thiadiazolyl groups. A suitable 5-membered heteroaromatic ring containing four nitrogen atoms is tetrazolyl. Suitable 6-membered heteroaromatic rings containing three nitrogen atoms include 1,2,4-triazine and 1,3,5-triazine.

The term "halogen" as used herein includes fluorine, chlorine, bromine and iodine, of which fluorine and chlorine are preferred.

As used herein the term "$C_{1-6}$alkoxy" includes methoxy and ethoxy groups, and straight-chained, branched and cyclic propoxy, butoxy, pentoxy and hexoxy groups, including cyclopropylmethoxy. Derived expressions such as "$C_{2-6}$alkenyloxy", "$C_{2-6}$alkynyloxy", "$C_{1-4}$alkoxy", "$C_{2-4}$alkenyloxy" and "$C_{2-4}$alkyloxy" should be construed in an analogous manner.

Four particular compounds which can be used are:
6-(1-methylimidazol-4-yl)methyloxy-3-(5-methylisoxazol-3-yl)-1,2,4-triazolo[3,4-a]phthalazine;
3-(5-methylisoxazol-3-yl)-6-(1-methyl-1,2,3-triazol-4-yl) methyloxy-1,2,4-triazolo[3,4-a]phthalazine;
3-(5-methylisoxazol-3-yl)-6-(2-pyridyl)-1,2,4-triazolo[3,4-a]phthalazine; and
3-(5-methylisoxazol-3-yl)-6-(1-methylimidazol-4-yl)-1,2,4-triazol-3-ylmethyloxy-1,2,4-triazolo[3,4-a]phthalazine.

The second of the above compounds is particularly favoured.

Further GABA$_A$ α5 inverse agonists which can be used in the present invention are suitable compounds disclosed in WO-A-9804560, WO-A-9818792, WO-A-9824435, WO-A-9906407, WO-A-9906399, WO-A-9906400 and WO-A-9906401.

Yet further GABA$_A$ α5 inverse agonists which can be used in the present invention are suitable compounds disclosed in EP-A-825193, WO-A-9639404, WOA-9734870, WO-A-9733889, U.S. Pat. Nos. 5,955,465, 5,095,015, 5,328,912, 5,604,235, 5,792,766, 5,908,932, WO-A-9200296, WO-A-9204351, WO-A-9206094, WO-A-9207853, WO-A-9511885, EP-A-738717, U.S. Pat. Nos. 5,130,430, 5,182,290, 5,182,386, 5,185,446, 5,212,310, 5,216,159, 5,243,049, 5,266,698, 5,286,860, 5,306,819, 5,312,822, 5,326,868, 5,367,077, 5,426,186, 5,451,585, 5,463,054, 5,473,073, 5,484,944, 5,510,480, 5,585,490, 5,606,059, 5,608,079, 5,610,299, 5,625,063, 5,637,724, 5,637,725, 5,668,283, 5,677,309, 5,693,801, 5,696,260, 5,723,462, 5,744,602, 5,744,603, 5,750,702, 5,763,609, 5,804,686, 5,817,813, 5,849,927, 5,910,590, 5,925,770, 5,936,095, WO-A-9734870, WO-A-9802420, WO-A-9802433, WO-A-9910347, WO-A-9918106, WO-A-9940092, WO-A-9943660, WO-A-9943661, WO-A-9943681, WO-A-9943682, WO-A-9200296, WO-A-9511885, WO-A-9405665, WO-A-9304066, WO-A-9726243, WO-A-9411374, WO-A-9415937, WO-A-9425461, WO-A-9733889, WO-A-9639404, WO-A-9207853, WO-A-9204351, WO-A-9322314, WO-A-9322681, WO-A-9426741, WO-A-9425463, WO-A-9206094 and WO-A-9426742.

The terms "inhibitor of cyclooxygenase-2", "cyclooxygenase-2 inhibitor" and "COX-2 inhibitor" as used herein embrace compounds which selectively inhibit cyclooxygenase-2 over cyclooxygenase-1. Employing the human whole blood COX-1 assay and the human whole blood COX-2 assay described in C. Brideau et al, *Inflamm. Res.* 45: 68–74 (1996), herein incorporated by reference, preferably, the compounds have a cyclooxygenase-2 IC$_{50}$ of less than about 2 μM in the human whole blood COX-2 assay, yet have a cyclooxygenase-1 IC$_{50}$ of greater than about 5 μM in the human whole blood COX-1 assay. Also preferably, the compounds have a selectivity ratio of cyclooxygenase-2 inhibition over cyclooxygenase-1 inhibition of at least 10, and more preferably of at least 40. The resulting selectivity may indicate an ability to reduce the incidence of common NSAID-induced side effects.

As explained in J. Talley, *Exp. Opin. Ther. Patents* (1997), 7(1), pp. 55–62, three distinct structural classes of selective COX-2 inhibitor compounds have been identified. One class is the methane sulfonanilide class of inhibitors, of which NS-398, flosulide, nimesulide and L-745,337 are example members.

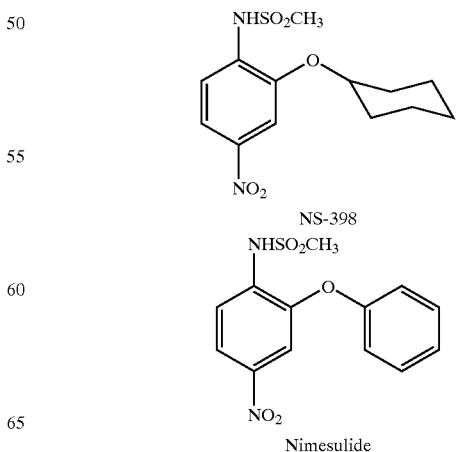

NS-398

Nimesulide

A second class is the tricyclic inhibitor class, which can be further divided into the sub-classes of tricyclic inhibitors with a central carbocyclic ring (examples include SC-57666, 1, and 2); those with a central monocyclic heterocyclic ring (examples include DuP 697, SC-58125, SC-58635, and 3, 4 and 5); and those with a central bicyclic heterocyclic ring (examples include 6, 7, 8, 9 and 10). Compounds 3, 4 and 5 are described in U.S. Pat. No. 5,474,995.

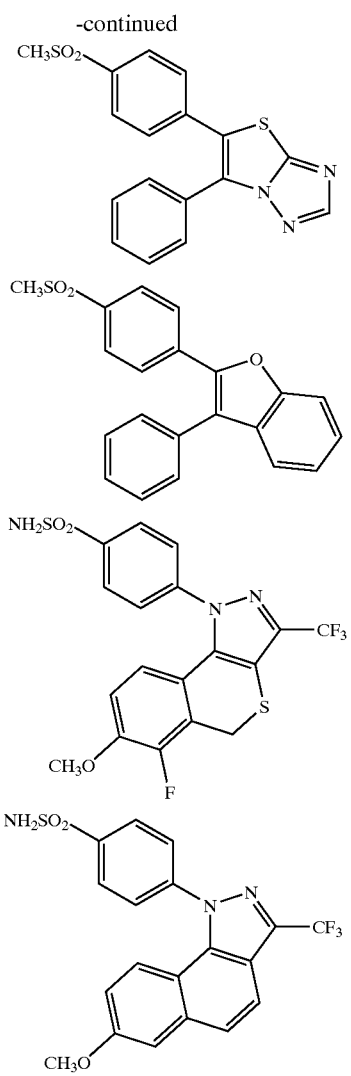

The third identified class can be referred to as those which are structurally modified NSAIDS, and includes L-761,066 and structure 11 as example members.

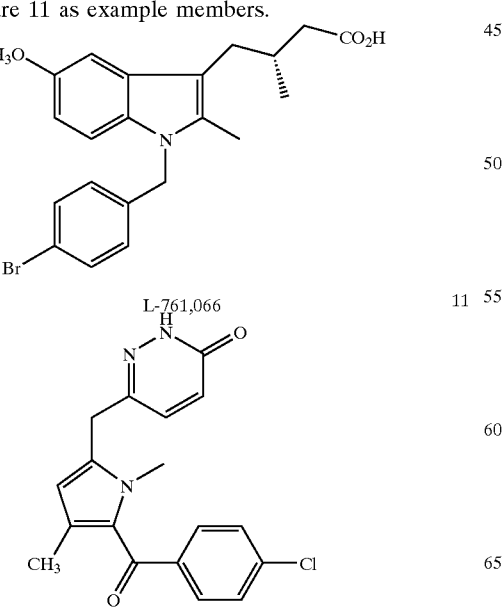

In addition to the structural classes, sub-classes, specific COX-2 inhibitor compound examples, and reference journal and patent publications described in the Talley publication which are all herein incorporated by reference, examples of compounds which selectively inhibit cyclooxygenase-2 have also been described in the following patent publications, all of which are herein incorporated by reference: U.S. Pat. Nos. 5,344,991, 5,380,738, 5,393,790, 5,409,944, 5,434,178, 5,436,265, 5,466,823, 5,474,995, 5,510,368, 5,536,752, 5,550,142, 5,552,422, 5,604,253, 5,604,260, 5,639,780; and International Patent Specification Nos. 94/13635, 94/15932, 94/20480, 94/26731, 94/27980, 95/00501, 95/15316, 96/03387, 96/03388, 96/06840; and International Publication No.'s WO 94/20480, WO 96/21667, WO 96/31509, WO 96/36623, WO 97/14691, WO 97/16435. Additional COX-2 inhibitor compounds which are included in the scope of this invention include:

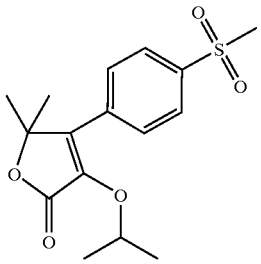

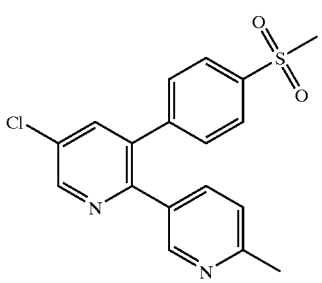

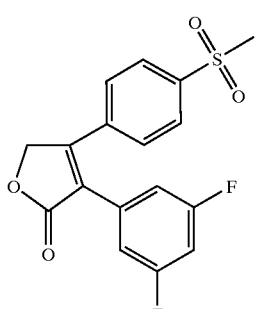

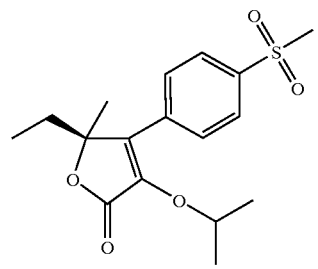

-continued

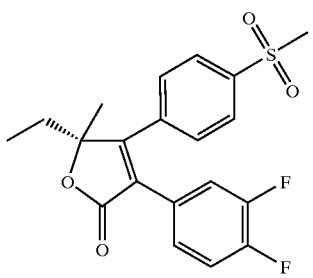
16

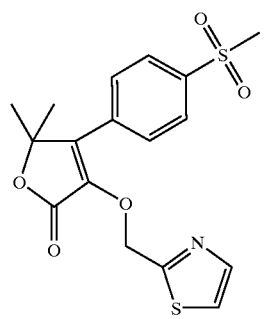
17

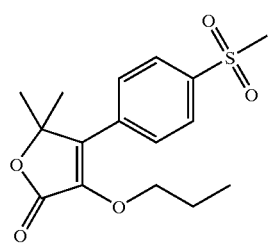
18

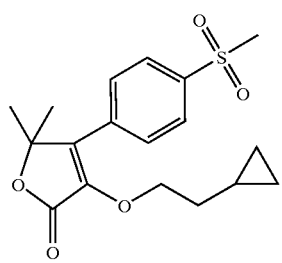
19

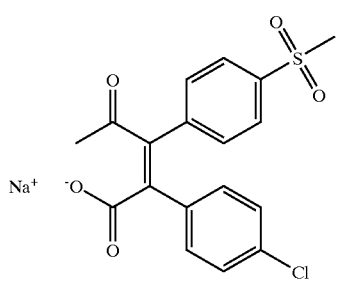
20

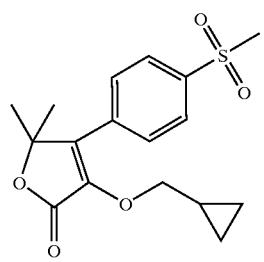
21

-continued

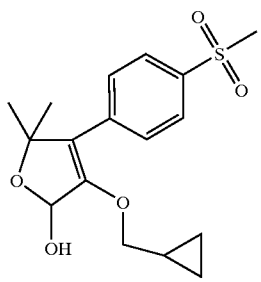
22

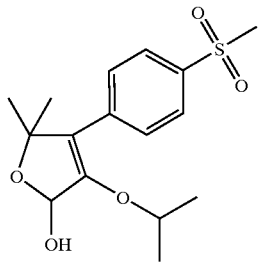
23

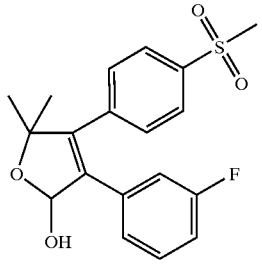
24

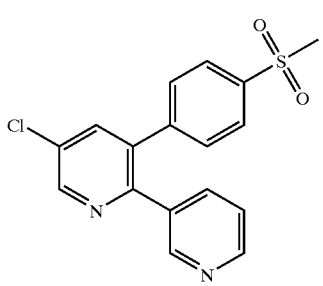
25

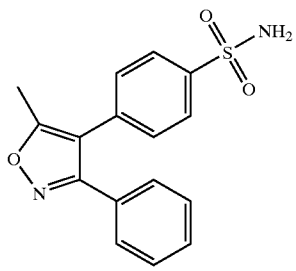
26

Some of the compounds above can also be identified by the following chemical names:

3: 3-phenyl-4-(4-(methylsulfonyl)phenyl)-2-(5H)-furanone;
4: 3-(3,4-difluorophenyl)-4-(4-(methylsulfonyl)phenyl)-2-(5H)-furanone;
5: 5,5-dimethyl-4-(4-(methylsulfonyl)phenyl)-3-(3-fluorophenyl)-5H-furan-2-one;
12: 5,5-dimethyl-4-(4-(methylsulfonyl)phenyl)-3-(2-propoxy)-5H-furan-2-one;
13: 5-chloro-3-(4-(methylsulfonyl)phenyl)-2-(2-methyl-5-pyridinyl)pyridine;

14: 2-(3,5-difluorophenyl)-3-(4-(methylsulfonyl)phenyl)-2-cyclopenten-1-one;
15: 5(S)-5-ethyl-5-methyl-4-(4-(methylsulfonyl)phenyl)-3-(2-propoxy)-5H-furan-2-one;
16: 5-ethyl-5-methyl-4-(4-(methylsulfonyl)phenyl)-3-(3,4-difluorophenyl)-5H-furan-2-one;
17: 3-((2-thiazolyl)methoxy)-4-(4-(methylsulfonyl)phenyl)-5,5-dimethyl-5H-furan-2-one;
18: 3-propyloxy-4-(4-(methylsulfonyl)phenyl)-5,5-dimethyl-5H-furan-2-one;
19: 3-(1-cyclopropylethoxy)-5,5-dimethyl-4-(4-methylsulfonyl)phenyl)-5H-furan-2-one;
20: sodium 2-(4-chlorophenyl)-3-(4-(methylsulfonyl)phenyl)-4-oxo-2-pentenoate;
21: 3-(cyclopropylmethoxy)-5,5-dimethyl-4-(4-(methylsulfonyl)phenyl)-5H-furan-2-one;
22: 3-(cyclopropylmethoxy)-5,5-dimethyl-4-(4-(methylsulfonyl)phenyl)-2,5-dihydrofuran-2-ol;
23: 3-isopropoxy-5,5-dimethyl-4-(4-(methylsulfonyl)phenyl)-2,5-dihydrofuran-2-ol;
24: 5,5-dimethyl-3-(3-fluorophenyl)-2-hydroxy-4-(4-(methylsulfonyl)phenyl)-2,5-dihydrofuran;
25: 5-chloro-3-(4-(methylsulfonyl)phenyl)-2-(3-pyridinyl)pyridine;
26: 4-(5-methyl-3-phenyl-4-isoxazolyl)benzenesulfonamide.

The following publications describe and/or provide methods for making the compounds as indicated: compounds 12, 15, 17, 18, 19 and 21, WO 97/14691; compounds 22, 23 and 24, WO 97/16435; compound 20, WO 96/36623; compound 14, U.S. Pat. No. 5,536,752; compound 16, U.S. Pat. No. 5,474,995. See Examples herein for compounds 13 and 25; compound 26, U.S. Pat. No. 5,633,272.

Also incorporated herein by reference are those compounds described in WO 96/41645 as having structural Formula I, shown below, and the definition and preferred definitions and species described therein:

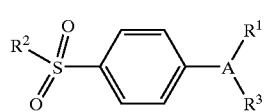

A

Particularly preferred compounds of formula (I) include:
5-(4-fluorophenyl)-1-[4-(methylsulfonyl)phenyl]-3-(trifluoromethyl)pyrazole;
4-(4-fluorophenyl)-5-[4-(methylsulfonyl)phenyl]-1-phenyl-3-(trifluoromethyl)pyrazole;
4-(5-(4-chlorophenyl)-3-(4-methoxyphenyl)-H-pyrazol-1-yl)benzenesulfonamide;
4-(3,5-bis(4-methylphenyl)-1H-pyrazol-1-yl)benzenesulfonamide;
4-(5-(4-chlorophenyl)-3-phenyl-1H-pyrazol-1-yl)benzenesulfonamide;
4-(3,5-bis(4-methoxyphenyl)-1H-pyrazol-1-yl)benzenesulfonamide;
4-(5-(4-chlorophenyl)-3-(4-methylphenyl)-1H-pyrazol-1-yl)benzenesulfonamide;
4-(5-(4-chlorophenyl)-3-(4-nitrophenyl)-1H-pyrazol-1-yl)benzenesulfonamide;
4-(5-(4-chlorophenyl)-3-(5-chloro-2-thienyl)-1H-pyrazol-1-yl)benzenesulfonamide;
4-(4-chloro-3,5-diphenyl-1H-pyrazol-1-yl)benzenesulfonamide;
4-(5-(4-chlorophenyl)-3-(trifluoromethyl)-1H-pyrazol-1-yl)benzenesulfonamide;
4-(5-phenyl)-3-(trifluoromethyl)-1H-pyrazol-1-yl)benzenesulfonamide;
4-(5-(4-fluorophenyl)-3-(trifluoromethyl)-1H-pyrazol-1-yl)benzenesulfonamide;
4-(5-(4-methoxyphenyl)-3-(trifluoromethyl)-1H-pyrazol-1-yl)benzenesulfonamide;
4-(5-(4-chlorophenyl)-3-(difluoromethyl)-1H-pyrazol-1-yl)benzenesulfonamide;
4-(5-(4-methylphenyl)-3-(trifluoromethyl)-1H-pyrazol-1-yl)benzenesulfonamide;
4-(4-chloro-5-(4-chlorophenyl)-3-(trifluoromethyl)-1H-pyrazol-1-yl)benzenesulfonamide;
4-(3-(difluoromethyl)-5-(4-methylphenyl)-1H-pyrazol-1-yl)benzenesulfonamide;
4-(3-(difluoromethyl)-5-phenyl-1H-pyrazol-1-yl)benzenesulfonamide;
4-(3-(difluoromethyl)-5-(4-methoxyphenyl)-1H-pyrazol-1-yl)benzenesulfonamide;
4-(3-cyano-5-(4-fluorophenyl)-1H-pyrazol-1-yl)benzenesulfonamide;
4-(3-(difluoromethyl)-5-(3-fluoro-4-methoxyphenyl)-1H-pyrazol-1-yl)benzenesulfonamide;
4-(5-(3-fluoro-4-methoxyphenyl)-3-(trifluoromethyl)-1H-pyrazol-1-yl)benzenesulfonamide;
4-(4-chloro-5-phenyl-1H-pyrazol-1-yl)benzenesulfonamide;
4-(5-(4-chlorophenyl)-3-(hydroxyphenyl)-1H-pyrazol-1-yl)benzenesulfonamide;
4-(5-(4-(N,N-dimethylamino)phenyl)-3-(trifluoromethyl)-1H-pyrazol-1-yl)benzenesulfonamide;
5-(4-fluorophenyl)-6-(4-(methylsulfonyl)phenyl)spiro[2.4]hept-5-ene;
4-(6-(4-fluorophenyl)spiro[2.4]hept-5-en-5-yl)benzenesulfonamide;
6-(4-fluorophenyl)-7-(4-(methylsulfonyl)phenyl)spiro [3.4]oct-6-ene;
5-(3-chloro-4-methoxyphenyl)-6-(4-(Methylsulfonyl)phenyl)spiro [2.4]hept-5-ene;
4-(6-(3-chloro-4-methoxyphenyl)spiro[2.4]hept-5-en-5-yl)benzenesulfonamide;
5-(3,5-dichloro-4-methoxyphenyl)-6-(4-(methylsulfonyl)phenyl)spiro[2.4]hept-5-ene;
5-(3-chloro-4-fluorophenyl)-6-(4-(methylsulfonyl)phenyl)spiro[2.4]hept-5-ene;
4-(6-(3,4-dichlorophenyl)spiro[2.4]hept-5-en-5-yl)benzenesulfonamide;
2-(3-chloro-4-fluorophenyl)-4-(4-fluorophenyl)-5-(4-methylsulfonylphenyl)thiazole;
2-(2-chlorophenyl)-4-(4-fluorophenyl)-5-(4-methylsulfonylphenyl)thiazole;
5-(4-fluorophenyl)-4-(4-methylsulfonylphenyl)-2-methylthiazole;
4-(4-fluorophenyl)-5-(4-methylsulfonylphenyl)-2-trifluoromethylthiazole;
4-(4-fluorophenyl)-5-(4-methylsulfonylphenyl)-2-(2-thienyl)thiazole;
4-(4-fluorophenyl)-5-(4-methylsulfonylphenyl)-2-benzylaminothiazole;
4-(4-fluorophenyl)-5-(4-methylsulfonylphenyl)-2-(1-propylamino)thiazole;
2-((3,5-dichlorophenoxy)methyl)-4-(4-fluorophenyl)-5-(4-(methylsulfonyl)phenyl)thiazole;
5-(4-fluorophenyl)-4-(4-methylsulfonylphenyl)-2-trifluoromethylthiazole;
1-methylsulfonyl-4-(1,1-dimethyl-4-(4-fluorophenyl)cyclopenta-2,4-dien-3-yl)benzene;
4-(4-(4-fluorophenyl)-1,1-dimethylcyclopenta-2,4-dien-3-yl)benzenesulfonamide;

5-(4-fluorophenyl)-6-(4-(methylsulfonyl)phenyl)spiro[2.4]hepta-4,6-diene;
4-(6-(4-fluorophenyl)spiro[2.4]hepta-4,6-dien-5-yl)benzenesulfonamide;
6-(4-fluorophenyl)-2-methoxy-5-(4-(methylsulfonyl)phenyl)-pyridine-3-carbonitrile;
2-bromo-6-(4-fluorophenyl)-5-(4-(methylsulfonyl)phenyl)-pyridine-3-carbonitrile;
6-(4-fluorophenyl)-5-(4-(methylsulfonyl)phenyl)-2-phenyl-pyridine-3-carbonitrile;
4-(2-(4-methylpyridin-2-yl)-4-(trifluoromethyl)-1H-imidazol-1-yl)benzenesulfonamide;
4-(2-(5-methylpyridin-3-yl)-4-(trifluoromethyl)-1H-imidazol-1-yl)benzenesulfonamide;
4-(2-(2-methylpyridin-3-yl)-4-(trifluoromethyl)-1H-imidazol-1-yl)benzenesulfonamide;
3-(1-(4-(methylsulfonyl)phenyl)-4-(trifluoromethyl)-1H-imidazol-2-yl)benzenesulfonamide;
2-(1-(4-(methylsulfonyl)phenyl)-4-(trifluoromethyl)-1H-imidazol-2-yl)pyridine;
2-methyl-4-(1-(4-(methylsulfonyl)phenyl)-4-(trifluoromethyl)-1H-imidazol-2-yl)pyridine;
2-methyl-6-(1-(4-(methylsulfonyl)phenyl)-4-(trifluoromethyl)-1H-imidazol-2-yl)pyridine;
4-(2-(6-methylpyridin-3-yl)-4-(trifluoromethyl)-1H-imidazol-1-yl)benzenesulfonamide;
2-(3,4-difluorophenyl)-1-(4-(methylsulfonyl)phenyl)-4-(trifluoromethyl)-1H-imidazole;
4-(2-(4-methylphenyl)-4-(trifluoromethyl)-1H-imidazol-1-yl)benzenesulfonamide;
2-(4-chlorophenyl)-1-(4-(methylsulfonyl)phenyl)-4-methyl-1H-imidazole;
2-(4-chlorophenyl)-1-(4-(methylsulfonyl)phenyl)-4-phenyl-1H-imidazole;
2-(4-chlorophenyl)-4-(4-fluorophenyl)-1-(4-(methylsulfonyl)phenyl)-1H-imidazole;
2-(3-fluoro-4-methoxyphenyl)-1-(4-(methylsulfonyl)phenyl)-4-(trifluoromethyl)-1H-imidazole;
1-(4-(methylsulfonyl)phenyl)-2-phenyl-4-trifluoromethyl-1H-imidazole;
2-(4-methylphenyl)-1-(4-(methylsulfonyl)phenyl)-4-trifluoromethyl-1H-imidazole;
4-(2-(3-chloro-4-methylphenyl)-4-(trifluoromethyl)-1H-imidazol-1-yl)benzenesulfonamide;
2-(3-fluoro-5-methylphenyl)-1-(4-(methylsulfonyl)phenyl)-4-(trifluoromethyl)-1H-imidazole;
4-(2-(3-fluoro-5-methylphenyl)-4-(trifluoromethyl)-1H-imidazol-1-yl)benzenesulfonamide;
2-(3-methylphenyl)-1-(4-(methylsulfonyl)phenyl)-4-(trifluoromethyl)-1H-imidazole;
4-(2-(3-methylphenyl)-4-(trifluoromethyl)-1H-imidazol-1-yl)benzenesulfonamide;
1-(4-(methylsulfonyl)phenyl)-2-(3-chlorophenyl)-4-(trifluoromethyl)-1H-imidazole;
4-(2-(3-chlorophenyl)-4-(trifluoromethyl)-1H-imidazol-1-yl)benzenesulfonamide;
4-(2-phenyl-4-(trifluoromethyl)-1H-imidazol-1-yl)benzenesulfonamide;
4-(2-(4-methoxy-3-chlorophenyl)-4-(trifluoromethyl)-1H-imidazol-1-yl)benzenesulfonamide;
1-allyl-4-(4-fluorophenyl)-3-(4-(methylsulfonyl)phenyl)-5-(trifluoromethyl)-1H-pyrazole;
4-(1-ethyl-4-(4-fluorophenyl)-5-(trifluoromethyl)-1H-pyrazol-3-yl)benzenesulfonamide;
N-phenyl-(4-(4-fluorophenyl)-3-(4-(methylsulfonyl)phenyl)-5-(trifluoromethyl)-1H-pyrazol-1-yl)acetamide;
ethyl (4-(4-fluorophenyl)-3-(4-(methylsulfonyl)phenyl)-5-(trifluoromethyl)-1H-pyrazol-1-yl)acetate;
4-(4-fluorophenyl)-3-(4-(methylsulfonyl)phenyl)-1-(2-phenylethyl)-1H-pyrazole;
4-(4-fluorophenyl)-3-(4-(methylsulfonyl)phenyl)-1-(2-phenylethyl)-5-(trifluoromethyl)pyrazole;
1-ethyl-4-(4-fluorophenyl)-3-(4-(methylsulfonyl)phenyl)-5-(trifluoromethyl)-1H-pyrazole;
5-(4-fluorophenyl)-4-(4-(methylsulfonyl)phenyl)-2-(trifluoromethyl)-1H-imidazole;
4-(4-(methylsulfonyl)phenyl)-5-(2-thiophenyl)-2-(trifluoromethyl)-1H-imidazole;
5-(4-fluorophenyl)-2-methoxy-4-(4-(methylsulfonyl)phenyl)-6-(trifluoromethyl)pyridine;
2-ethoxy-5-(4-fluorophenyl)-4-(4-(methylsulfonyl)phenyl)-6-(trifluoromethyl)pyridine;
5-(4-fluorophenyl)-4-(4-(methylsulfonyl)phenyl)-2-(2-propynyloxy)-6-(trifluoromethyl)pyridine;
2-bromo-5-(4-fluorophenyl)-4-(4-(methylsulfonyl)phenyl)-6-(trifluoromethyl)pyridine;
4-(2-(3-chloro-4-methoxyphenyl)-4,5-difluorophenyl)benzenesulfonamide;
1-(4-fluorophenyl)-2-(4-(methylsulfonyl)phenyl)benzene;
5-difluoromethyl-4-(4-(methylsulfonyl)phenyl)-3-phenylisoxazole;
4-(3-ethyl-5-phenylisoxazol-4-yl)benzenesulfonamide;
4-(5-difluoromethyl-3-phenylisoxazol-4-yl)benzenesulfonamide;
4-(5-hydroxymethyl-3-phenylisoxazol-4-yl)benzenesulfonamide;
4-(5-methyl-3-phenylisoxazol-4-yl)benzenesulfonamide;
1-(2-(4-fluorophenyl)cyclopenten-1-yl)-4-(methylsulfonyl)benzene;
1-(2-(4-fluoro-2-methylphenyl)cyclopenten-1-yl)-4-(methylsulfonyl)benzene;
1-(2-(4-chlorophenyl)cyclopenten-1-yl)-4-(methylsulfonyl)benzene;
1-(2-(2,4-dichlorophenyl)cyclopenten-1-yl)-4-(methylsulfonyl)benzene;
1-(2-(4-trifluoromethylphenyl)cyclopenten-1-yl)-4-(methylsulfonyl)benzene;
1-(2-(4-methylthiophenyl)cyclopenten-1-yl)-4-(methylsulfonyl)benzene;
1-(2-(4-fluorophenyl)-4,4-dimethylcyclopenten-1-yl)-4-(methylsulfonyl)benzene;
4-(2-(4-fluorophenyl)-4,4-dimethylcyclopenten-1-yl)benzenesulfonamide;
1-(2-(4-chlorophenyl)-4,4-dimethylcyclopenten-1-yl)-4-(methylsulfonyl)benzene;
4-(2-(4-chlorophenyl)-4,4-dimethylcyclopenten-1-yl)benzenesulfonamide;
4-(2-(4-fluorophenyl)cyclopenten-1-yl)benzenesulfonamide;
4-(2-(4-chlorophenyl)cyclopenten-1-yl)benzenesulfonamide;
1-(2-(4-methoxyphenyl)cyclopenten-1-yl)-4-(methylsulfonyl)benzene;
1-(2-(2,3-difluorophenyl)cyclopenten-1-yl)-4-(methylsulfonyl)benzene;
4-(2-(3-fluoro-4-methoxyphenyl)cyclopenten-1-yl)benzenesulfonamide;
1-(2-(3-chloro-4-methoxyphenyl)cyclopenten-1-yl)-4-(methylsulfonyl)benzene;
4-(2-(3-chloro-4-fluorophenyl)cyclopenten-1-yl)benzenesulfonamide;
4-(2-(2-methylpyridin-5-yl)cyclopenten-1-yl)benzenesulfonamide;
ethyl 2-(4-(4-fluorophenyl)-5-(4-(methylsulfonyl)phenyl)oxazol-2-yl)-2-benzyl-acetate;

2-(4-(4-fluorophenyl)-5-(4-(methylsulfonyl)phenyl)oxazol-2-yl)acetic acid;

2-(tert-butyl)-4-(4-fluorophenyl)-5-(4-(methylsulfonyl) phenyl)oxazole;

4-(4-fluorophenyl)-5-(4-(methylsulfonyl)phenyl)-2-phenyloxazole;

4-(4-fluorophenyl)-2-methyl-5-(4-(methylsulfonyl)phenyl) oxazole; and 4-(5-(3-fluoro-4-methoxyphenyl)-2-trifluoromethyl-4-oxazolyl)benzenesulfonamide;

or a pharmaceutically acceptable salt thereof

Especially preferred COX-2 inhibitors are rofecoxib and celecoxib, supremely rofecoxib.

Within the terms of the invention, the NSAIDs include, but are not restricted to, the following chemical agents that inhibit prostaglandin synthesis primarily by their activity against the enzyme cyclooxygenase:

(1) Arylcarboxylic acids: salicylic acid, acetylsalicyclic acid, diflunisal, choline magnesium trisalicylate, salicylate, benorylate, flufenamic acid, mefenamic acid, meclofenamic acid, niflumic acid;

(2) Arylalkanoic acids: diclofenac, fenclofenac, alclofenac, fentiazac, ibuprofen, flurbiprofen, ketoprofen, naproxen, fenoprofen, fenbufen, suprofen, indoprofen, tiaprofenic acid, benoxaprofen, pirprofen, tolmetin, zomepirac, clopinac, indomethacin, sulindac;

(3) Enolic acids: phenylbutazone, oxyphenbutazone, azapropazone, feprazone, piroxicam, isoxicam, sudoxicam.

By estrogen is meant a compound of formula:

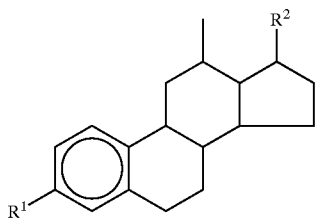

wherein $R^1$ and $R^2$ are independently chosen from hydrogen, hydroxyl, methyl, methylester, acetate, ethylether, benzoate, benzyl ether, glucoronide, valerate, cyclopentylpropionate, sulfate sodium salt, propionate, hemisuccinate, palmitate, sodium phosphate, enanthate, glucoronide sodium salt, stearate, triethyl ammonium salt and cyprionate or $R^2$ may alternatively be divalent and chosen from oxygen, dimethyl ketal and 17-hydroxy-17-ethynyl. The estrogen may be α or β estrogen, ie. the group $R^2$ may be in either optical configuration. α and β estrogen, particular β estrogen are preferred. Synthetic estrogens such as raloxifene or conjugated estrogens such as premarin are also within the meaning of the term estrogen.

Vitamin E is known to include several forms of alpha tocopherol. As used herein the term "vitamin E" refers to any form of vitamin E that exists (which includes esterified forms) or any combination thereof. One form of vitamin E is the d-alpha-tocopherol which is isolated from natural sources and consists solely of the naturally occurring stereoisomer RRR-alpha-tocopherol. Another form is the d,l-alpha-tocopherol also known as all racemic-alpha-tocopherol which is a mixture of 8 stereoisomers produced during its synthesis. In general, the naturally occurring d-alpha form and its esters are preferred over the synthetic forms due to the higher biological potency and the absence of synthetic stereoisomers. It is preferred that the purity of the vitamin E exceed 97% and be essentially free of synthetic stereoisomers. Typical esters include alkyl esters such as $C_1$–$C_4$ alkyl esters (e.g., d-alpha-tocopheryl acetate, and succinate) and polyethylene glycol succinate.

Thus in the first embodiment the present invention also provides a pharmaceutical composition comprising a COX-2 inhibitor, an inverse agonist of the $GABA_A$ α5 receptor subtype and a pharmaceutically acceptable carrier.

There is also provided a kit of parts comprising a first pharmaceutical composition comprising a COX-2 inhibitor and a first pharmaceutically acceptable carrier and a second pharmaceutical composition comprising an inverse agonist of the $GABA_A$ α5 receptor subtype and a second pharmaceutically acceptable carrier for simultaneous, sequential or separate administration.

There is further provided a combination of a COX-2 inhibitor and an inverse agonist of the $GABA_A$ α5 receptor subtype for use in a method of treatment of the human body, particularly for the treatment of a neurodegenerative disorder with associated cognitive deficit such as Alzheimer's Disease or Parkinson's disease, or of a cognitive deficit arising from a normal process such as aging or of an abnormal process such as injury. The combination is particularly beneficial in the treatment of Alzheimer's Disease.

There is also provided the use of a combination of a COX-2 inhibitor and an inverse agonist of the $GABA_A$ α5 receptor subtype in the manufacture of a medicament for the treatment of a neurodegenerative disorder such as Alzheimer's Disease or Parkinson's disease, or of a cognitive deficit arising from a normal process such as aging or of an abnormal process such as injury. The treatment of Alzheimer's Disease is particularly preferred.

There is also disclosed a method of treatment of a subject suffering from a neurodegenerative disorder, such as Alzheimer's Disease or Parkinson's disease, or a cognitive deficit arising from a normal process such as aging or an abnormal process such as injury, which comprises administering to that subject a therapeutically effective amount of a combination of a COX-2 inhibitor and an inverse agonist of the $GABA_A$ $α_5$ receptor subtype. The treatment of Alzheimer's Disease is particularly preferred.

Thus in the second embodiment the present invention provides a pharmaceutical composition comprising an NSAID, an inverse agonist of the $GABA_A$ α5 receptor subtype and a pharmaceutially acceptable carrier.

There is also provided a kit of parts comprising a first pharmaceutial composition comprising an NSAID and a first pharmaceutically acceptable carrier and a second pharmaceutical composition comprising an inverse agonist of the $GABA_A$ α5 receptor subtype and a second pharmaceutically acceptable carrier for simultaneous, sequential or separate administration.

There is further provided a combination of an NSAID and an inverse agonist of the $GABA_A$ α5 receptor subtype for use in a method of treatment of the human body, particularly for the treatment of a neurodegenerative disorder with associated cognitive deficit such as Alzheimer's disease or Parkinson's disease, or of a cognitive deficit arising from a normal process such as ageing or or an abnormal process such as injury. The combination is particularly beneficial in the treatment of Alzheimer's disease.

There is also provided the use of a combination of an NSAID and an inverse agonist of the $GABA_A$ α5 receptor subtype in the manufacture of a medicament for the treatment of a neurodegenerative disorder such as Alzheimer's disease or Parkinson's disease, or of a cognitive deficit arising from a normal process such as ageing or of an abnormal process such as injury. The treatment of Alzheimer's disease is particularly preferred.

There is also disclosed a method of treatment of a subject suffering from a neurodegenerative disorder, such as Alzheimer's disease or Parkinson's disease, or a cognitive deficit arising from a normal process such as ageing or an abnormal process such as injury, which comprises administering to that subject a therapeutically effective amount of a combination of an NSAID and an inverse agonist of the $GABA_A$ α5 receptor subtype. The treatment of Alzheimer's disease is particularly preferred.

Thus in the third embodiment the present invention provides a pharmaceutical composition comprising an estrogen, an inverse agonist of the $GABA_A$ α5 receptor subtype and a pharmaceutically acceptable carrier.

There is also provided a kit of parts comprising a first pharmaceutical composition comprising an estrogen and a first pharmaceutically acceptable carrier and a second pharmaceutical composition comprising an inverse agonist of the $GABA_A$ α5 receptor subtype and a second pharmaceutically acceptable carrier for simultaneous, sequential or separate administration.

There is further provided a combination of an estrogen and an inverse agonist of the $GABA_A$ α5 receptor subtype for use in a method of treatment of the human body, particularly for the treatment of a neurodegenerative disorder with associated cognitive deficit such as Alzheimer's disease or Parkinson's disease or of a cognitive deficit arising from a normal process such as ageing or of an abnormal process such as injury. The combination is particularly beneficial in the treatment of Alzheimer's disease.

There is also provided the use of a combination of an estrogen and an inverse agonist of the $GABA_A$ α5 receptor subtype in the manufacture of a medicament for the treatment of a neurodegenerative disorder such as Alzheimer's desease or Parkinson's disease, or of a cognitive deficit arising from a normal process such as ageing or of an abnormal process such as injury. The treatment of Alzheimer's disease is particularly preferred.

There is also disclosed a method of treatment of a subject suffering from a neurodegenerative disorder, such as Alzheimer's disease or Parkinson's disease, or a cognitive deficit arising from a normal process such as ageing or an abnormal process such as injury, which comprises administering to that subject a therapeutically effective amount of a combination of an estrogen and an inverse agonist of the $GABA_A$ α5 receptor subtype. The treatment of Alzheimer's disease is particularly preferred.

Thus in the fourth embodiment the present invention provides a pharmaceutical composition comprising vitamin E, an inverse agonist of the $GABA_A$ α5 receptor subtype and a pharmaceutically acceptable carrier.

There is also provided a kit of parts comprising a first pharmaceutical composition comprising vitamin E and a first pharmaceutically acceptable carrier and a second pharmaceutical composition comprising an inverse agonist of the $GABA_A$ α5 receptor subtype and a second pharmaceutically acceptable carrier for simultaneous, sequential or separate administration.

There is further provided a combination of vitamin E and an inverse agonist of the $GABA_A$ α5 receptor subtype for use in a method of treatment of the human body, particularly for the treatment of a neurodegenerative disorder with associated cognitive deficit such as Alzheimer's disease or Parkinson's disease or of a cognitive deficit arsing from a normal process such as ageing or of an abnormal process such as injury. The combination is particularly beneficial in the treatment of Alzheimer's disease.

There is also provided the use of a combination of vitamin E and an inverse agonist of the $GABA_A$ α5 receptor subtype in the manufacture of a medicament for the treatment of a neurodegenerative disorder such as Alzheimer's disease or Parkinson's disease, or of a cognitive deficit arising from a normal process such as ageing or of an abnormal process such as injury. The treatment of Alzheimer's disease is particularly preferred.

There is also disclosed a method of treatment of a subject suffering from a neurodegenerative disorder, such as Alzheimer's disease or Parkinson's disease, or a cognitive deficit arising from a normal process such as ageing or an abnormal process such as injury, which comprises administering to that subject a therapeutically effective amount of a combination of vitamin E and an inverse agonist of the $GABA_A$ α5 receptor subtype. The treatment of Alzheimer's disease is particularly preferred.

The pharmaceutical compositions of the present invention are preferably in unit dosage forms such as tablets, pills, capsules, powders, granules, sterile parenteral solutions or suspensions, metered aerosol or liquid sprays, drops, ampoules, transdermal patches, auto-injector devices or suppositories; for oral, parenteral, intranasal, sublingual or rectal administration, or for administration by inhalation or insufflation. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums or surfactants such as sorbitan monooleate, polyethylene glycol, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of each active ingredient of the present invention. Typical unit dosage forms contain from 1 to 100 mg, for example 1, 2, 5, 10, 25, 50 or 100 mg, of each active ingredient. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the novel compositions of the present invention may be incorporated for administration orally or by injection include aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinylpyrrolidone or gelatin.

For the treatment of a neurodegenerative condition, a suitable dosage level is about 0.01 to 250 mg/kg per day, preferably about 0.01 to 100 mg/kg per day, and especially about 0.01 to 5 mg/kg of body weight per day of each active ingredient. The compounds may be administered on a regimen of 1 to 4 times per day. In some cases, however, dosage outside these limits may be used.

The synergistic effect of the combination of the present invention can be shown, for example, by comparing the combined dosage of the combination with dosages of the same amount of each of the active ingredients separately on subjects using the Mini-Mental State Examination (MMSE) as described in Folstein and Folstein J. Psychiat. Res., 1975, 12, 189–198 or a variant thereof as discussed in Tombaugh and McIntyre, JAGS, 1992, 40, 922–935.

The following Example illustrates the preparation of a preferred GABA$_A$ α5 selective inhibitor of use in the present invention.

Intermediate 1

6-Chloro-3-(5-Methylisoxazol-3-yl)-1,2,4-triazolo[3,4-a]phthalazine a) 1-Chloro-4-hydrazinophthalazine 1,4-Dichlorophthalazine (20.0g, 0.100 mol) was added to a boiling solution of hydrazine monohydrate (37.3 ml, 0.765 mol) in ethanol (500 ml) and the mixture heated at reflux for 0.5 h. The mixture was cooled to room temperature and the solid collected by filtration and washed with ether. The material was taken with n-butanol and ammonia solution (sp. gr. 0.91) and heated until the solid dissolved. The organic layer was separated, evaporated in vacuo and the residue azeotroped with xylene (×2) and dried in vacuo to give the title-hydrazine (11.5 g, 59%), $^1$H NMR (250 MHz, d$^6$DMSO) δ7.84–8.04 (3H, m, Ar—H), 8.20 (1H, m, Ar—H); MS (ES$^+$) m/e 194 [MH]$^+$.

b) 5-Methylisoxazole-3-carboxylic acid

A mixture of acetonylacetone (10 g, 88 mmol) and nitric acid (sp. gr. 1.42)/water (2:3) (50 ml) was cautiously brought to reflux under a stream of nitrogen and boiled for 1 h. The solution was cooled to room temperature and aged overnight. The resultant solid was collected by filtration, washed with chilled water (2×7 ml) and hexane, and dried in vacuo to give the title-acid (4.4 g, 40%), $^1$H NMR (CDCl$_3$) δ2.50 (3H, d, J=0.8 Hz, Me), 6.41 (1H, d, J=0.8 Hz, Ar—H).

c) 6-Chloro-3-(5-Methylisoxazol-3-yl)-1,2,4-triazolo[3,4-a]phthalazine

5-Methylisoxazole-3-carboxylic acid (5.24 g, 41.3 mmol), bis(2-oxo-3-oxazolidinyl)phosphinic chloride (10.5 g, 41.2 mmol) and triethylamine (11.5 ml, 82.5 mmol) were added successively to a stirred suspension of 1-chloro-4-hydrazinophthalazine (8.00 g, 41.2 mmol) in dichloromethane (1 l) at 0° C. under nitrogen. The mixture was stirred at 0° C. for 2 h and at room temperature overnight. The solvent was evaporated in vacuo, the residue triturated with water and the solid filtered off, washed with hexane and dried in vacuo to give the ketohydrazine (11 g), MS (ES$^+$) m/e 304 [MH]$^+$. A solution of the ketohydrazine (11 g) and triethylamine hydrochloride (2.2 g, 20% w/w) in xylene (500 ml) was heated at reflux for 3 h. The mixture was cooled to room temperature and the solvent evaporated in vacuo. The residue was dissolved in dichloromethane, washed with water (×2), dried (MgSO$_4$) and evaporated in vacuo, and the solid recrystallised (dichloromethane/hexane) to give the title-compound (6.8 g, 58%), $^1$H NMR (360 MHz, CDCl$_3$) δ2.59 (3H, s, Me), 6.90 (1H, s, Ar—H), 7.95 (1H, m, Ar—H), 8.07 (1H, m, Ar—H), 8.34 (1H, m, Ar—H), 8.78 (1H, s, Ar—H); MS (ES$^+$) m/e 286 [MH]$^+$.

Reference Example 1

3-(5-Methylisoxazol-3-yl)-6-(2-pyridyl)methyloxy-1,2,4-triazolo[3,4-a]phthalazine Sodium hydride (244 mg of a 60% dispersion in oil, 6.10 mmol) was added to a stirred solution of 2-pyridylcarbinol (470 mg, 4.27 mmol) in DMF (60 ml) at room temperature under nitrogen and the mixture stirred for 0.25 h. After this time, Intermediate 1 (1160 mg, 4.07 mmol) was added and the mixture stirred for 2 h. The solvent was removed in vacuo and the residue dissolved in dichloromethane, washed with water (×2), dried (MgSO$_4$) and evaporated in vacuo. Flash chromatography on silica gel eluting with 3% methanol/dichloromethane followed by recrystallisation (dichloromethane/hexane) gave the title-product (640 mg, 44%), mp 234–236° C.; $^1$H NMR (360 MHz, CDCl$_3$) δ2.59 (3H, d, J=0.8 Hz, Me), 5.77 (2H, s, CH$_2$), 6.82 (1H, d, J=0.8 Hz, Ar—H), 7.30 (1H, m, Ar—H), 7.74–7.85 (3H, m, Ar—H), 7.95 (1H, m, Ar—H), 8.33 (1H, d, J=7.8 Hz, Ar—H), 8.64–8.72 (2H, m, Ar—H); MS (ES$^+$) m/e 359 [MH]$^+$; Anal. Found. C, 62.93; H, 3.56; N, 22.94. C$_{19}$H$_{14}$N$_6$O$_2$ 0.05 (CH$_2$Cl$_2$) requires C, 63.10; H, 3.92; N, 23.17%.

Reference Example 2

6-(6-Bromopyridin-2-yl)methyloxy-3-(5-methylisoxazol-3-yl)-1,2,4-triazolo[3,4-a]phthalazine The title-compound was prepared from Intermediate 1 and 2-bromopyridine-6-methanol (*Tetrahedron Lett.*, 1996, 50, 2537) following the procedure given for Reference Example 1. The product was isolated by addition of water to the reaction mixture and the resulting precipitate was filtered off. Flash chromatography on silica gel, eluting with ethyl acetate, and recrystallisation (ethyl acetate-methanol) gave the title-phthalazine, mp 247.5–249° C.; $^1$H NMR (360 MHz, CDCl$_3$) δ2.61 (3H, d, J=0.7 Hz, Me), 5.73 (2H, s, CH$_2$), 6.82 (1H, d, J=0.7 Hz, Ar—H), 7.48 (1H, d, J=7.8 Hz, Ar—H), 7.63 (1H, t, J=7.7 Hz, Ar—H), 7.76 (1H, d, J=7.4 Hz, Ar—H), 7.84 (1H, t, J=8.4 Hz, Ar—H), 7.98 (1H, t, J=8.4 Hz, Ar—H), 8.31 (1H, d, J=8.5 Hz, Ar—H), 8.70 (1H, d, Ar—H); MS (ES$^+$) m/e 437 [MH]$^+$; Anal. Found C, 52.27; H, 2.85; N, 19.14. C$_{19}$H$_{13}$N$_6$O$_2$ Br. 0.1 (H$_2$O) requires C, 51.98; H, 3.03; N, 18.60%.

Intermediate 2

6-Hydroxy-3-(5-Methylisoxazol-3-yl)-1,2,4-triazolo[3,4-a]phthalazine

A solution of sodium hydroxide (0.67 g, 17 mmol) in water (7.5 ml) was added to a stirred solution of Intermediate 1 (1.0 g, 3.5 mmol) in dioxane (37.5 ml) and the mixture heated at reflux for 4 h. The solvent was evaporated in vacuo and the residue partitioned between water and diethyl ether. The aqueous layer was separated, washed with ether (×1) and then acidified with 2N hydrochloric acid until pH2 was attained. The solid which precipitated out of solution was filtered off and the aqueous filtrate extracted with dichloromethane (×3). The combined extracts were dried (MgSO$_4$) and evaporated in vacuo and combined with the precipitate to give the title-product (0.45 g, 48%), $^1$H NMR (250 MHz, d$^6$-DMSO) δ2.58 (3H, d, J=0.7 Hz, Me), 7.07 (1H, d, J=0.9 Hz, Ar—H), 7.94 (1H, m, Ar—H), 8.08 (1H, m, Ar—H), 8.24 (1H, d, J=7.4 Hz, Ar—H), 8.54 (1H, d, J 7.4 Hz, Ar—H), 13.32 (1H, br s, NH); MS (ES$^+$) m/e 268 [MH]$^+$

Reference Example 3

3-(5-Methylisoxazol-3-yl)-6-(1H-1,2,3-triazol-5-yl)
methyloxy-1,2,4-triazolo[3,4-a]phthalazine a) 5-Formyl-1-[2-(trimethylsilyl)ethoxy]methyl-1,2,3-triazole n-Butyl lithium (6.8 ml of a 1.6M solution in hexanes, 10.9 mmol) was added dropwise over 0.08 h to a stirred solution of 1-[2-(trimethyl-silyl)ethoxy]methyl-1,2,3-triazole (J. Heterocycl. Chem., 1992, 29, 1203) (2.077 g, 10.42 mmol) in THF (30 ml) at −78° C. under nitrogen. The solution was allowed to warm to −60° C. over 0.67 h, then recooled to −78° C. and DMF (0.9 ml, 11.6 mmol) added. The mixture was allowed to warm to room temperature and stirred for 16.5 h. Saturated ammonium chloride solution (50 ml) was added and the reaction mixture extracted with diethyl ether (3×80 ml). The combined ethereal extrants were dried (MgSO$_4$), evaporated in vacuo, and the residue chromatographed on silica gel, eluting with 30% ethyl acetate/hexane, to give the title-triazole (1.713 g, 72%), $^1$H NMR (360 MH$_2$, CDCl$_3$) δ0.01 (9H, S, Me$_3$Si), 0.92–0.99 (2H, m, CH$_2$), 3.64–3.69 (2H, m, CH$_2$), 6.05 (2H, s, CH$_2$), 8.31 (1H, s, Ar—H), 10.12 (1H, s, CHO).

b) 5-Hydroxymethyl-1-[2-(trimethylsilyl)ethoxy]methyl-1,2,3-triazole

Sodium borohydride (0.284 g, 7.51 mmol) was added to a stirred solution of the preceding triazole (1.704 g, 7.495 mmol) in methanol (8 ml) at 0° C. under nitrogen. The mixture was stirred at 0° C. for 0.5 h and at room temperature for 0.5 h. Water was added and the mixture partitioned between dichloromethane and saturated brine. The aqueous layer was separated and further extracted with dichloromethane (×2). The combined organic layers were dried ((MgSO$_4$) and evaporated in vacuo and the residue chromatographed on silica gel, eluting with 70% ethyl acetate/hexane, to give the title-product (1.34 g, 78%), $^1$H NMR (360 MHz, CDCl$_3$) δ0.00 (9H, s, Me$_3$Si), 0.90–0.95 (2H, m, CH$_2$), 3.58–3.63 (2H, m, CH$_2$), 4.84 (2H, s, CH$_2$), 5.80 (2H, s, CH$_2$), 7.68 (1H, s, Ar—H).

c) 3-(5-Methylisoxazol-3-yl)-6-{1-[2-(trimethylsilyl)ethoxy]methyl-1,2,3-triazol-5-yl}methyloxy-1,2,4-triazolo[3,4-a]phthalazine The title-coinpound was prepared from Intermediate 1 and the preceding alcohol following the procedure described for Example 10, 360 MHz (360 MHz, CDCl$_3$) δ0.00 (9H, s, Me$_3$Si), 0.88–0.93 (2H, m, CH$_2$), 2.63 (3H, s, Me), 3.61–3.66 (2H, m, CH$_2$), 5.92 (2H, s, CH$_2$), 5.97 (2H, s, CH$_2$), 6.89 (1H, s, Ar—H), 7.86 (1H, m, Ar—H), 8.02 (1H, t, J 7.7 Hz, Ar—H), 8.18 (1H, s, Ar—H), 8.23 (1H, d, J=8.0 Hz, Ar—H), 8.76 (1H, d, J=8.0 Hz, Ar—H); MS (ES$^+$) m/e 479 [MH]$^+$.

d) 3-(5-Methylisoxazol-3-yl)-6-(1H-1,2,3-triazol-5-yl)methyloxy-1,2,4-triazolo[3,4-a]phthalazine A mixture of the preceding product, ethanol (10 ml) and 2N HCl (20 ml) was heated at 50° C. for 15.25 h. The solution was basified to pH 12 with saturated sodium carbonate solution and the solvents evaporated in vacuo. The residue was azeotroped with ethanol (×2) and chromatographed on silica gel, eluting with 0–4% methanol/dichloromethane (gradient elution), to give the title-product, $^1$H NMR (400 MHz, CDCl$_3$) δ2.65 (3H, s, Me), 5.73 (2H, s, CH$_2$), 7.02 (1H, s, Ar—H), 7.87 (1H, t, J=7.8 Hz, Ar—H), 7.99–8.03 (2H, m, 2 of Ar—H), 8.24 (1H, d, J=8.2 Hz, Ar—H) 8.72 (1H, d, J=7.9 Hz, Ar—H); MS (ES$^+$) m/e 349 [MH]$^+$.

EXAMPLE 1

3-(5-Methylisoxazol-3-yl)-6-(1-methyl-1,2,3-triazol-5-yl)methyloxy-1,2,4-triazolo[3,4-a]phthalazine, 3-(5-methylisoxazol-3-yl)-6-(2-methyl-1,2,3-triazol-4-yl)methyloxy-1,2,4-triazolo[3,4-a]phthalazine and 3-(5-methylisoxazol-3-yl)-6-(1-methyl-1,2,3-triazol-4-yl)methyloxy-1,2,4-triazolo[3,4-a]phthalazine Lithium hexamethyldisilazide (1.63 ml of a 1M solution in THF, 1.63 mmol) was added dropwise to a stirred solution of 3-(5-methylisoxazol-3-yl)-6-(1H-1,2,3-triazol-5-yl)methyloxy-1,2,4-triazolo[3,4-a]phthalazine (241 mg, 0.626 mmol) prepared as in Reference Example 3 in DMF (50 ml) at −31° C. under nitrogen. The mixture was warmed to −23° C. over 1.5 h, methyl iodide (0.10 ml, 1.6 mmol) added dropwise and the reaction mixture allowed to warm to room temperature overnight. Water was added and the solvent evaporated in vacuo. The residue was partitioned between dichloromethane and water and the aqueous phase separated and re-extracted with dichloromethane (×1). The combined organic extrants were washed with brine (×1), dried (MgSO$_4$) and evaporated in vacuo. Chromatography of the residue on silica gel, eluting with 0–5% methanol/dichloromethane (gradient elution), followed by preparative HPLC (YMC Sil column, 250×20 mm) eluting with 5% methanol/1-chlorobutane, separated the triazole isomers: Least polar isomer (HPLC solvent system): 3-(5-methylisoxazol-3-yl)-6-(2-methyl-1,2,3-triazol-4-yl)methyloxy-1,2,4-triazolo[3,4-a]phthalazine $^1$H NMR (400 MHz, CDCl$_3$) δ2.59 (3H, s, Me), 4.21 (3H, s, Me), 5.73 (2H, s, CH$_2$), 6.89 (1H, s, Ar—H), 7.79 (1H, m, Ar—H), 7.94 (1H, m, Ar—H), 8.10 (1H, s, Ar—H), 8.22 (1H, d, J=8.0 Hz, Ar—H), 8.67 (1H, d, J=8.0 Hz, Ar—H); MS (ES$^+$) m/e 363 [MH]$^+$.
Intermediate polarity isomer: 3-(5-methylisoxazol-3-yl)-6-(1-methyl-1 2,3-triazol-4-yl)methyloxy-1,2,4-triazolo[3,4-a]phthalazine $^1$H NMR (400 MHz, CDCl$_3$) δ2.60 (3H, s, Me), 4.09 (3H, s, Me), 5.78 (2H, s, CH$_2$), 6.90 (1H, d, J=0.8 Hz, Ar—H), 7.80 (1H, m, Ar—H), 7.94 (1H, m, Ar—H), 8.25 (1H, d, J=8.0 Hz, Ar—H), 8.65 (1H, d, J=8.0 Hz, Ar—H), 8.73 (1H, s, Ar—H); MS (ES$^+$) m/e 363 [MH]$^+$.
Most polar isomer (HPLC solvent system): 3-(5-methylisoxazol-3-yl)-6-(1-methyl-1,2,3-triazol-5-yl)methyloxy-1,2,4-triazolo[3,4-a]phthalazine $^1$H NMR (400 MHz, CDCl$_3$) δ2.56 (3H, s, Me), 4.19 (3H, s, Me), 5.76 (2H, s, CH$_2$), 6.82 (1H, s, Ar—H), 7.80 (1H, m, Ar—H), 7.96 (1H, m, Ar—H), 8.04 (1H, s, Ar—H), 8.12 (1H, d, J=8.8 Hz, Ar—H), 8.67 (1H, d, J=8.0 Hz, Ar—H); MS (ES$^+$) m/e 363 [MH]$^+$.

In a further aspect the present invention provides a combination of 3-(5-methylisoxazol-3-yl)-6-(1-methyl-1,2,3-triazol-4-yl)methyloxy-1,2,4-triazolo[3,4-a]phthalazine and COX-2 inhibitor for separate, simultaneous or sequential administration.

The COX-2 inhibitor is preferably a selective COX-2 inhibitor such as rofecoxib or celecoxib. Rofecoxib is preferred. The selective COX-2 inhibitor preferably binds to COX-2 over COX-1 in a whole blood assay at a ratio of greater than 5:1 and more preferably of greater than 20:1.

In the combination 3-(5-methylisoxazol-3-yl)-6-(1-methyl-1,2,3-triazol-4-yl)methyloxy-1,2,4-triazolo[3,4-a]phthalazine is administered in the dosage ranges given above. The selective COX-2 inhibitor is administered at from 1 mg to 600 mg per day. In the case of rofecoxib the dosage range is favourably from 5 mg to 100 mg and preferably 12.5 mg to 50 mg per day. In the case of celecoxib the dosage range is preferably from 200 to 600 mg per day.

The combination may be provided in any conventional formulation known in the art suitable for separate, sequential or simultaneous administration. The two active ingredients may be provided in individual formulations or together in a single formulation, for example a tablet.

A further aspect of the present invention thus provides a method of treatment of a subject suffering a cognition deficit, such as from Alzheimer's Disease, which comprises separate, sequential or simultaneous administration to that subject of a cognition enhancing amount of a combination of 3-(5-methylisoxazol-3-yl)-6-(1-methyl-1,2,3-triazol-4-yl) methyloxy-1,2,4-triazolo[3,4-a]phthalazine and a COX-2 inhibitor.

In another aspect the present invention provides a combination of 3-(5-methylisoxazol-3-yl)-6-(1-methyl-1,2,3-triazol-4-yl)methyloxy-1,2,4-triazolo[3,4-a]phthalazine and an NSAID for separate, sequential or simultaneous administration.

In the combination the 3-(5-methylisoxazol-3-yl)-6-(1-methyl-1,2,3-triazol-4-yl)methyloxy-1,2,4-triazolo[3,4-a] phthalazine and the NSAID are administered in the dosage ranges given above.

The formulation of the combination may be as described herein.

A further aspect of the present invention thus provides a method of treatment of a subject suffering from a cognition deficit, such as from Alzheimer's disease, which comprises separate, sequential or simultaneous administration to that subject of a cognition enhancing amount of 3-(5-methylisoxazol-3-yl)-6-(1-methyl-1,2,3-triazol-4-yl) methyloxy-1,2,4-triazolo[3,4-a]phthalazine and an NSAID.

In another aspect the present invention provides a combination of 3-(5-methylisoxazol-3-yl)-6-(1-methyl-1,2,3-triazol-4-yl)methyloxy-1,2,4-triazolo[3,4-a]phthalazine and an estrogen compound for separate, sequential or simultaneous administration.

The estrogen compound is any estrogen compound used in hormone replacement therapy, such as estrogen.

In the combination 3-(5-methylisoxazol-3-yl)-6-(1-methyl-1,2,3-triazol-4-yl)methyloxy-1,2,4-triazolo[3,4-a] phthalazine is administered in the dosage ranges given above. The estrogen compound is administered at from 0.05 to 10 mg per day.

The formulation of the combination may be as described herein.

A further aspect of the present invention thus provides a method of treatment of a subject suffering from a cognition deficit, such as from Alzheimer's Disease, which comprises separate, sequential or simultaneous administration to that subject of a cognition enhancing amount of 3-(5-methylisoxazol-3-yl)-6-(1-methyl-1,2, 3-triazol-4-yl) methyloxy-1,2,4-triazolo[3,4-a]phthalazine and an estrogen compound.

In a further aspect the present invention provides a combination of 3-(5-methylisoxazol-3-yl)-6-(1-methyl-1,2, 3-triazol-4-yl)methyloxy-1,2,4-triazolo[3,4-a]phthalazine and Vitamin E for separate, sequential or simultaneous administration.

Vitamin E is administered in any conventional form such as the free acid, acetate or succinate.

In the combination 3-(5-methylisoxazol-3-yl)-6-(1-methyl-1,2,3-triazol-4-yl)methyloxy-1,2,4-triazolo[3,4-a] phthalazine is administered in the dosage ranges given above. Vitamin E is administered at from 50 to 24000 IU per day.

The formulation of the combination may be as described herein.

A further aspect of the present invention thus provides a method of treatment of a subject suffering from a cognition deficit, such as from Alzheimer's Disease, which comprises administering separately, sequentially or simultaneously to that subject a cognition enhancing amount of a combination of 3-(5-methylisoxazol-3-yl)-6-(1-methyl-1,2,3-triazol-4-yl)methyloxy-1,2,4-triazolo[3,4-a]phthalazine and Vitamin E.

Especially preferred COX-2 inhibitors of use in the present invention are identified using the following one or more of the following selection criteria:

(i) Determine the affinity for human COX-2 in whole cell assay; select compounds with $ID_{50} \leq 40$ nM, and preferably $ID_{50} \leq 20$ nM.

(ii) Determine oral bioavailability of compounds by pharmacokinetic analysis or inhibition of carrageenan-induced paw oedema in rats following oral administration. Select compounds with $ED_{50} \leq 5$ mg/kg p.o., and preferably $ED_{50} \leq 2.5$ mg/kg p.o.

(iii) Determine the ability of compounds to induce gastric ulceration or increase in faecal $^{51}Cr$ excretion. Select compounds that have no adverse gastrointestinal effects at $\geq 100$ mg/kg p.o., when administered up to two times a day.

(iv) Determine antinociceptive effects of compounds in carrageenan-induced hyperalgesia in rats; select compounds with $ED_{50} \leq 5$ mg/kg p.o., and preferably $ED_{50} \leq 2.5$ mg/kg p.o.

(v) Determine the affinity for COX-2 in human whole blood assay which is used as an index for biochemical efficacy in the clinic and select compounds with $IC_{50} \leq 1$ $\mu$M for inhibition of $PGE_2$.

The following examples illustrate pharmaceutical compositions according to the invention.

These formulations may be prepared with separate active ingredients or with a combination of active ingredients in one composition. In such combined preparations, the ratio of the COX-2 inhibitor, NSAID, estrogen or vitamin E and the $GABA_A$ $\alpha 5$ inverse agonist will depend upon the choice of active ingredients.

Composition Example 1

|  | Amount (mg) per tablet | | |
| --- | --- | --- | --- |
| $GABA_A$ $\alpha 5$ inverse agonist | 50.0 | 100.0 | 300.0 |
| Microcrystalline cellulose | 80.0 | 80.0 | 80.0 |
| Modified food corn starch | 80.0 | 80.0 | 80.0 |
| Lactose | 189.5 | 139.5 | 139.5 |
| Magnesium Stearate | 0.5 | 0.5 | 0.5 |

The active ingredient, cellulose, lactose and a portion of the corn starch are mixed and granulated with 10% corn starch paste. The resulting granulation is sieved, dried and blended with the remainder of the corn starch and the magnesium stearate. The resulting granulation is then compressed into tablets containing 50 mg, 100 mg and 300 mg of the $GABA_A$ $\alpha 5$ inverse agonist per tablet.

Composition Example 2

|  | Amount (mg) per tablet | | |
|---|---|---|---|
| GABA$_A$ α5 inverse agonist | 50.0 | 100.0 | 300.0 |
| COX-2 inhibitor | 20.0 | 20.0 | 20.0 |
| Microcrystalline cellulose | 80.0 | 80.0 | 80.0 |
| Modified food corn starch | 80.0 | 80.0 | 80.0 |
| Lactose | 169.5 | 119.5 | 119.5 |
| Magnesium Stearate | 0.5 | 0.5 | 0.5 |

The active ingredients, cellulose, lactose and a portion of the corn starch are mixed and granulated with 10% corn starch paste. The resulting granulation is sieved, dried and blended with the remainder of the corn starch and the magnesium stearate. The resulting granulation is then compressed into tablets containing 20 mg of the COX-2 inhibitor and 50 mg, 100 mg and 300 mg of the GABA$_A$ α5 inverse agonist per tablet.

Composition Example 3

| Wet granulated tablet composition | | | | |
|---|---|---|---|---|
|  | Amount (mg) per tablet | | | |
| COX-2 Inhibitor | 25 | 12.5 | 10 | 5 |
| Microcrystalline cellulose | 79.7 | 86 | 87.2 | 89.7 |
| Lactose monohydrate | 79.7 | 86 | 87.2 | 89.7 |
| Hydroxypropyl cellulose | 6 | 6 | 6 | 6 |
| Croscarmellose sodium | 8 | 8 | 8 | 8 |
| Iron oxide | 0.6 | 0.6 | 0.6 | 0.6 |
| Magnesium stearate | 1 | 1 | 1 | 1 |

Tablet dose strengths of between 5 and 25 mg can be accomodated by varying total tablet weight, and the ratio of the first three ingredients. Generally it is preferable to maintain a 1:1 ratio for microcrystalline cellulose:lactose monohydrate.

Composition Example 4

| Directly compressed tablet composition | | | | |
|---|---|---|---|---|
|  | Amount (mg) per tablet | | | |
| COX-2 Inhibitor | 25 | 12.5 | 10 | 5 |
| Microcrystalline cellulose | 106.9 | 113.2 | 42.5 | 45 |
| Lactose anhydrate | 106.9 | 113.2 | 42.5 | 45 |
| Crosmellose sodium | 7.5 | 7.5 | 4 | 4 |
| Magnesium stearate | 3.7 | 3.7 | 1 | 1 |

Tablet dose strengths of between 5 and 25 mg can be accomodated by varying total tablet weight, and the ratio of the first three ingredients. Generally it is preferable to maintain a 1:1 ratio for microcrystalline cellulose:lactose monohydrate.

Composition Example 5

| Hard gelatin capsule composition | |
|---|---|
|  | Amount (mg) per capsule |
| COX-2 Inhibitor | 25 |
| Microcrystalline cellulose | 37 |
| Lactose anhydrate | 37 |
| Magnesium stearate | 1 |
| Hard gelatin capsule | 1 capsule |

Capsule dose strengths of between 1 and 50 mg can be accomodated by varying total fill weight, and the ratio of the first three ingredients. Generally it is preferable to maintain a 1:1 ratio for microcrystalline cellulose:lactose monohydrate.

Composition Example 6

| Oral solution | |
|---|---|
|  | Amount per 5 ml dose |
| COX-2 Inhibitor | 50 mg |
| Polyethylene oxide 400 | to 5 ml |

Solution dose strengths of between 1 and 50 mg/5 ml can be accomodated by varying the ratio of the two ingredients.

Composition Example 7

| Oral suspension | |
|---|---|
|  | Amount per 5 ml dose |
| COX-2 Inhibitor | 100 mg |
| Polyvinylpyrrolidone | 150 mg |
| Polyoxyethylene sorbitan monolaurate | 2.5 mg |
| Benzoic acid | 10 mg |
| sorbitol solution (70%) | to 5 ml |

Suspension dose strengths of between 1 and 50 mg/5 ml can be accomodated by varying the ratio of the first two ingredients.

Composition Example 8

| Intravenous infusion | |
|---|---|
|  | Amount per 200 ml dose |
| COX-2 inhibitor | 1 mg |
| Polyethylene oxide 400 | 0.2 mg |
| Sodium chloride | 1.8 mg |
| Purified water | to 200 ml |

It will be understood that the cox-2 inhibitor in any of the above composition examples can be replaced with an NSAID, estrogen or vitamin E.

What is claimed is:
1. A pharmaceutical composition comprising:
    i) a combination including an NSAID and an inverse agonist of the GABA$_A$ α5 receptor subtype; and
    ii) a pharmaceutically acceptable carrier.

2. The combination according to claim 1, wherein said combination is effective for use in a method of treatment of the human body.

3. A method of treatment of a subject suffering from a neurodegenerative disorder or a cognitive deficit said method comprises a step of administering to that subject a therapeutically effective amount of the combination according to claim 1.

4. A kit of parts comprising a first pharmaceutial composition comprising an NSAID and a first pharmaceutically acceptable carrier and a second pharmaceutical composition comprising an inverse agonist of the $GABA_A$ $\alpha 5$ receptor subtype and a second pharmaceutically acceptable carrier for simultaneous, sequential or separate administration.

* * * * *